(12) United States Patent
Singer et al.

(10) Patent No.: US 8,252,271 B2
(45) Date of Patent: Aug. 28, 2012

(54) HAIR STYLING COMPOSITIONS CONTAINING A SILICONE ELASTOMER AND A NON-AQUEOUS POLAR SOLVENT

(75) Inventors: Jim M. Singer, South Orange, NJ (US); Jisook Baek, Princeton, NJ (US)

(73) Assignee: L'Oreal S.A., Paris (FR)

( * ) Notice: Subject to any disclaimer, the term of this patent is extended or adjusted under 35 U.S.C. 154(b) by 1595 days.

(21) Appl. No.: 11/649,409

(22) Filed: Jan. 4, 2007

(65) Prior Publication Data

US 2007/0204871 A1    Sep. 6, 2007

Related U.S. Application Data

(60) Provisional application No. 60/779,132, filed on Mar. 3, 2006.

(51) Int. Cl.
*A61Q 5/12* (2006.01)
(52) U.S. Cl. .................................................... 424/70.12
(58) Field of Classification Search ........................ None
See application file for complete search history.

(56) References Cited

U.S. PATENT DOCUMENTS

| | | | |
|---|---|---|---|
| 4,699,146 A | 10/1987 | Sieverding | |
| 4,764,363 A * | 8/1988 | Bolich, Jr. | 424/47 |
| 4,983,418 A | 1/1991 | Murphy et al. | |
| 5,100,658 A | 3/1992 | Bolich, Jr. et al. | |
| 5,104,646 A | 4/1992 | Bolich, Jr. et al. | |
| 5,106,609 A | 4/1992 | Bolich, Jr. et al. | |
| 5,120,531 A | 6/1992 | Wells et al. | |
| 5,601,810 A * | 2/1997 | Mausner | 424/70.7 |
| 5,654,362 A | 8/1997 | Schulz, Jr. et al. | |
| 6,060,547 A | 5/2000 | Canter et al. | |
| 6,200,554 B1 * | 3/2001 | Yeoh et al. | 424/70.12 |
| 6,248,336 B1 * | 6/2001 | McDermott | 424/401 |
| 6,451,298 B1 | 9/2002 | Decoster et al. | |
| 6,475,500 B2 | 11/2002 | Vatter et al. | |
| 6,488,918 B2 * | 12/2002 | Hess et al. | 424/62 |
| 6,548,074 B1 * | 4/2003 | Mohammadi | 424/401 |
| 6,589,510 B2 | 7/2003 | Kalbfleisch et al. | |
| 6,602,495 B2 | 8/2003 | Bergmann et al. | |
| 2003/0165546 A1 | 9/2003 | Resch et al. | |
| 2003/0170308 A1 | 9/2003 | Cleary et al. | |
| 2005/0048016 A1 | 3/2005 | Lebreton et al. | |
| 2005/0063916 A1 | 3/2005 | Ishii et al. | |
| 2005/0232886 A1 | 10/2005 | Walter et al. | |
| 2006/0120984 A1 | 6/2006 | Decoster et al. | |
| 2006/0140896 A1 | 6/2006 | Decoster et al. | |

FOREIGN PATENT DOCUMENTS

| | | |
|---|---|---|
| CA | 2323945 | 4/2001 |
| CA | 2324034 | 4/2001 |
| EP | 1093806 | 4/2001 |
| EP | 1093807 | 4/2001 |
| EP | 1093809 | 4/2001 |
| EP | 1314415 | 5/2003 |
| EP | 1437119 | 7/2004 |
| EP | 1481660 | 12/2004 |
| EP | 1493421 | 1/2005 |
| EP | 1792640 | 6/2007 |
| JP | 2001-097831 | 4/2001 |
| JP | 2003-040740 | 2/2003 |
| JP | 2003-342130 | 12/2003 |
| WO | WO 99/63952 | 12/1999 |

OTHER PUBLICATIONS

European Communication dated Nov. 20, 2009 in corresponding European Patent Application No. 07300841.9.
European Search Report dated Aug. 7, 2009 in corresponding European Patent Application No. 07300841.9.

* cited by examiner

*Primary Examiner* — Tracy Vivlemore
*Assistant Examiner* — Jennifer Berrios
(74) *Attorney, Agent, or Firm* — L'Oreal USA Products Inc.

(57) ABSTRACT

A process for styling a keratinous material involving providing a composition containing at least one silicone elastomer, at least one non-aqueous polar solvent, optionally, at least one styling polymer, optionally, at least one emulsifying agent; and a cosmetically acceptable co-solvent, other than the non-aqueous polar solvent; and applying said composition onto the keratinous material.

13 Claims, No Drawings

HAIR STYLING COMPOSITIONS CONTAINING A SILICONE ELASTOMER AND A NON-AQUEOUS POLAR SOLVENT

STATEMENT OF RELATED APPLICATIONS

This application is a non-provisional application of, and claims benefit to, U.S. Provisional Application No. 60/779,132, filed Mar. 3, 2006.

BACKGROUND OF THE INVENTION

Various hair cosmetic compositions differ in their desirable efficacies based on the needs of the consumer. One important element of such compositions is their ability to hold or set hair in place. Many consumers seek hair styling products which would give medium to light hold and at the same time, enable them to re-fix or re-style or re-shape their hair without the need to re-apply the product and/or heat. The resulting feel and texture of the hair after application is also an important element of a such products. While different technologies and products exist that have these qualities, there is still a need for improvement in these areas. One way of achieving this is through the careful selection and levels of ingredients in the hair styling compositions in order to impart the desired levels of hold, reshapability properties and texture on hair.

Thus, the object of this invention is to provide a process of styling hair using a composition that would give medium to light hold and allow one to re-fix or re-style or re-shape the hair without re-applying the composition and/or heat, and at the same time, give a unique soft and dry feel to the hair.

BRIEF SUMMARY OF THE INVENTION

The present invention is directed to a process for styling a keratinous material involving the steps of:
 (a) providing a composition containing:
  i at least one silicone elastomer;
  ii at least one non-aqueous polar solvent;
  iii optionally, at least one styling polymer;
  iv optionally, at least one emulsifying agent; and
  v a cosmetically acceptable co-solvent, other than (ii), and
 (b) applying said composition onto the keratinous material.

The present invention is also directed to a hair styling cosmetic composition which, after application, provides a medium to light hair styling hold with a soft and dry feel to the hair, the composition containing:
 (a) at least one silicone elastomer;
 (b) at least one non-aqueous polar solvent;
 (c) at least one styling polymer;
 (d) optionally, at least one emulsifying agent; and
 (e) a cosmetically acceptable co-solvent, other than (b),
wherein (b) is present in an amount of at least about 20% by weight based on the weight of the composition.

DETAILED DESCRIPTION

Other than in the operating examples, or where otherwise indicated, all numbers expressing quantities of ingredients and/or ratios of ingredients are to be understood as being modified in all instances by the term "about".

The present invention is directed to a process for styling a keratinous material involving the steps of providing a hair styling composition containing at least one silicone elastomer, at least one non-aqueous polar solvent, optionally, at least one styling polymer, optionally, at least one emulsifying agent, and a cosmetically acceptable co-solvent other than the non-aqueous polar solvent; and applying said composition onto the keratinous material.

The present invention also relates to compositions for hair such as sprays, mousses, styling gels, leave-on conditioners, permanent waving compositions, hair care products, hair treatment products, and hair styling products comprising, at least one silicone elastomer, at least one non-aqueous polar solvent, optionally, at least one styling polymer, optionally, at least one emulsifying agent, and a cosmetically acceptable co-solvent other than the non-aqueous polar solvent; and applying said composition onto hair.

It is to be understood that both the foregoing general description and the following detailed description are exemplary and explanatory only, and are not restrictive of the invention.

The term "hair styling" as used herein refers to styling or fixing hair into a desired configuration, such as imparting a style or temporary curl or set (straight or curly) to human hair and retaining or maintaining (grooming, restyling) a desired set or curl configuration. The term "hair styling composition", encompasses products comprising at least one silicone elastomer that are applied to wet or dry or semi-dry hair before, during or after configuring the hair into the shape (curly or straight) desired, without limitation as to product form. The terms hair "styling" and hair "fixative" agents as used herein, refer collectively to hair styling agents that are hair fixatives and film formers and which are topically applied to the hair to actively contribute to the ease of styling and/or holding of a section of hair, and to maintain the restylability or refixability or reshapability of the hair or section of hair. Therefore, the present invention on hair styling compositions can include hair styling, hair fixative, and hair grooming products that conventionally are applied to wet or dry or semi-dry hair in the form of gels, rinses, emulsions (oil-in-water, water-in-oil or multiphase), such as lotions and creams, pomades, sprays (pressurized or non-pressurized), spritzes, mousses, foams, shampoos, solids, such as sticks, semisolids and the like, or are applied from a hair styling aid having the hair styling composition impregnated therein or coated thereon, to leave the hair styling agent in contact with the hair for some period until removed, as by washing.

The term "medium to light hold" as used herein refers to imparting a styling or hold to hair or a section of hair without firmly styling the hair, maintaining the finished hair style or hair styling for long hours, and restyling or refixing or reshaping the hair by combing it with fingers or a brush.

The term "dry feel" as used herein refers to the keratinous material treated with the composition of the present invention as dry to the touch or not greasy nor slippery, while at the same still feeling smooth and silky.

The term "cosmetically acceptable co-solvent" as used herein is known to one of ordinary skill in the art, and may comprise, for example, water and/or at least one organic solvent.

The term "reshapeable" as used herein means to provide a hair styling or hair style and/or hold that can be restored or modified with or without the use of additional material or application of heat. Additional heat and/or styling or styling compositions may be used, if hair becomes unduly wet or dirty, is excessively combed, brushed or manipulated, washed, or when hair is to be dramatically restyled. At least some of the compositions in accordance with the invention should be reshapeable, as judged by a professional hair stylist of ordinary skill, for at least 4 hours and up to 24 hours or more after initial application. Preferably and merely for example, in order to restore or modify the hairstyle in case of "drooping" or loss of styling (dishevelment), no new materials, such as water or any form of fixing agent, or heat are required. Other terms, which may be synonymous with reshapeable, include repositionable, remoldable, restyleable, rearrangeable, and remodellable. The term "reshapeable" also means to provide a hairstyle that can retain or hold a desired shape or configuration until water, heat, time and/or physical contact destroys the desired shape or configuration.

The cosmetic compositions and methods of the present invention can comprise, consist of, or consist essentially of the essential elements and limitations of the invention described herein, as well as any additional or optional ingredients, components, or limitations described herein or any otherwise useful ingredient found in personal care compositions intended for application to keratinous materials.

The composition of the present invention may be in any form. For example, it may be a paste, a solid or a cream. The composition of the invention may be transparent or clear, including for example, a composition without pigments. The composition can also be a molded composition or cast as a stick or a dish. The composition in one embodiment is a solid such as a molded stick or a poured stick.

Silicone Elastomer

Silicone elastomers useful in accordance with the invention include, without limitation, compounds generally known as polyorganosiloxanes. These may be made of cross-linked elastomeric polyorganosiloxanes described in U.S. Pat. No. 5,654,362, the disclosure of which is incorporated herein by reference.

The elastomers are by definition crosslinked, the degree of which can be vary depending on the elastic properties of the polymer that are desired. Cross-linking materials may be hydrophilic (ethylene oxide and propylene oxide, for example), hydrophobic (dimethicone, vinyl dimethicone, alkyl, etc.) or combinations thereof.

The silicone elastomers, are typically dissolved in a suitable solvent, either prior to their introduction into the composition of the invention, or in situ within the composition. Examples of suitable solvents, include, but are not limited to, volatile and non-volatile silicones, volatile and non-volatile alcohols, volatile and non-volatile esters, volatile and non-volatile hydrocarbons and mixtures thereof. Preferred silicone elastomers for use herein are elastomer/solvent blends, also referred to as "gels", having an elastomer to solvent ratio of from about 1:100 to about 1:1, more preferably from about 1:50 to about 1:5. Preferably the silicone elastomer/solvent blend has a viscosity of no more than 7,500,000 centipoise, more preferably no more than 500,000 centipoise. Preferably the silicone elastomer blend has a viscosity of at least than 1,000 centipoise, more preferably at least 10,000 centipoise.

Examples of silicone elastomers which can be used according to the invention include KSG6 (Shin-Etsu), Trefil E-505C or Trefil E-506C, now known as DC 9506 (dimethicone/vinyldimethicone crosspolymer, Dow-Corning and Toray), Gransil SR-CYC, SR DMF10, SR-DC556 (Grant Industries), KSP 100 and 200 series and KMP series (Shin Etsu), KSG15, KSG17, KSG16, and KSG18 (Shin-Etsu), Gransil SR 5CYC gel, Gransil SR DMF 10 gel, Gransil SR DC556 gel, SF 1204 and JK 113 (General Electric), DC 9040 (cyclomethicone and dimethicone crosspolymer blend, Dow Corning), DC 9701 (dimethicone/vinyl dimethicone cross-polymer coated with silica, Dow Corning), SFE 839, (cyclomethicone and dimethicone/vinyldimethicone crosspolymer blend), and Velvesil (General Electric). A mixture of these commercial products may also be used.

The at least one silicone elastomer is preferably a nonemulsifying silicone elastomer. Preferred elastomers in accordance with the present invention include Dow Corning DC 9506 Silicone elastomer powder. It is preferably used as a powder. DC9506 is a dimethicone/vinyldimethicone crosspolymer which is generally spherical. Another preferred second elastomer is Dow Corning 9701 cosmetic powder, which is a spherical silicone elastomer powder coated with silica (dimethicone/vinyl dimethicone cross-polymer and silica).

Nonemulsifying silicone elastomers are described in U.S. patent application Publication No. U.S. 2003/0165546A1, and specifically, paragraph nos. 109 and 110 which is also hereby incorporated by reference. Also useful are the elastomers listed in U.S. Pat. No. 6,475,500 to Vatter et al., issued Nov. 5, 2002, the elastomers from which are hereby incorporated by reference.

It is not required that the elastomers be spherical, but those which are and which have properties similar to DC 9506 and DC 9701 in terms of oil and sebum adsorption, silky, floating feel, with a similar "bounce" or "cushion" may be used, so long as they are compatible. Preferably, the elastomer is used in the form of a powder, preferably one with an aerated bulk density of about 0.18 or lower. It is swellable in a silicone solvent such as D5 and has a spongy or rubber-like feel. Adding the D5 solvent in a sufficient amount such that the elastomer swells but no free solvent is left results in some unique properties of the elastomer and the surface being treated with the elastomer. Generally, upon the application of pressure, even when sufficient solvent is present, such as when manipulated by one's fingers over the palm of one's hand, spreading is efficient, silky and smooth. Often, it is accompanied with a generally "floating" or "gliding" sensation that occurs without balling up or pilling. The generally spherical shape of the elastomer appears to contribute to this sensation. Upon application of a composition of the present invention onto a keratinous material, the presence of the pre-swelled elastomer contributes to a soft, dry feel on the surface of the keratinous material.

The silicone elastomer gel or powder is present in the compositions of the present invention at a level of from 0.1% to 25% by weight, preferably at a level of from 1.0% to 10% by weight, and even more preferably at a level from 0.5% to 5% by weight, based on the weight of the composition.

Non-Aqueous Polar Solvent

A variety of nonaqueous polar organic solvents are suitable for use in the composition of the present invention. Examples thereof are as follows.

Polyols

Polyols are suitable nonaqueous polar organic solvents. For purposes of this specification, polyols are defined as compounds which contain three or more hydroxyl groups per molecule. Examples of suitable polyols include fructose, glucamine, glucose, glucose glutamate, glucuronic acid, glycerin, 1,2,6hexanetriol, hydroxystearyl methylglucanine, inositol, lactose, malitol, mannitol, methyl gluceth-10, methyl gluceth-20, methyl glucose dioleate, methyl glucose sesquicaprylate/sesquicaprate, methyl glucose sesquicocoate, methyl glucose sesquiisostearate, methyl glucose sesquilaurate, methyl glucose sesquistearate, phytantriol, riboflavin, sorbeth-6, sorbeth-20, sorbeth-30, sorbeth-40, sorbitol, sucrose, thioglycerin, xylitol, and mix thereof. An especially preferred polyol is glycerin.

Polymeric or Monomeric Ethers

Also suitable as the nonaqueous polar organic solvent are homopolymeric or block copolymeric liquid ethers. Polymeric ethers are preferably formed by polymerization of monomeric alkylene oxides, generally ethylene or propylene oxides. Examples of such polymeric ethers include PEG, PPG, and derivatives thereof.

Other examples of suitable polymeric ethers include polyoxypropylene polyoxyethylene block copolymers. Such compounds are sold under the CTFA name Meroxapol 105, 108, 171, 172, 174, 178, 251, 252, 254, 255, 258, 311, 312, and 314.

Mono- and Dihydric Alcohols

Also suitable for use as to the nonaqueous polar organic solvent are mono- and dihydric alcohols of the general formula $R(OH)_n$ where n is 1 or 2 and R is a substituted or unsubstituted saturated $C_{2-10}$, preferably $C_{1-8}$ alkyl, or a substituted or unsubstituted alicyclic, bicyclic, or aromatic ring, with the substituents selected from halogen, alkoxy, hydroxy, and so on. Examples of suitable alcohols include monohydric alcohols such as ethanol, isopropanol, hexyldecanol, benzyl alcohol, propyl alcohol, and isopropyl alcohol, as well as dihydric alcohols such as hexylene glycol, diethylene glycol, ethylene glycol, propylene glycol, 1,2-butylene glycol, triethylene glycol, dipropylene glycol, and mixtures thereof.

Sorbitan Derivatives

Sorbitan derivatives, which are defined as ethers or esters of sorbitan, are also suitable polar solvents. Examples of suitable sorbitan derivatives are the Polysorbates, which are defined as stearate esters of sorbitol and sorbitan anhydrides, such as Polysorbate 20, 21, 40, 60, 61, 65, 80, 81, and 85. Also suitable are fatty esters of hexitol anhydrides derived from sorbitol, such as sorbitan trioleate, sorbitan tristearate, sorbitan sesquistearate, sorbitan stearate, sorbitan palmitate, sorbitan oleate, and mixtures thereof.

Preferred non-aqueous polar solvents may be chosen from may be chosen from glycols and glycol ethers.

The non-aqueous polar solvent is present in the compositions of the present invention at a level of from 10% to 75% by weight, preferably at a level of from 15% to 60% by weight, and even more preferably at a level from 20% to 50% by weight, based on the weight of the composition.

Styling Polymer

The styling polymers used in the present invention which may be chosen from nonionic, anionic, cationic, and amphoteric polymers and mixtures thereof. The styling polymer may additionally be halogenated, in particular fluorinated.

The styling polymers can be used in solubilized form or else in the form of dispersions of solid polymer particles (latex or pseudo-latex).

The cationic styling polymers which can be used according to the present invention can be selected from polymers containing primary, secondary, tertiary and/or quaternary amine groups forming part of the polymer chain or linked directly to it and having a molecular weight of between 500 and approximately 5,000,000 and preferably between 1000 and 3,000,000.

The anionic styling polymers that are generally used are polymers containing groups derived from carboxylic, sulphonic or phosphoric acid and have a weight-average molecular weight of between approximately 500 and 5,000,000.

The carboxylic groups are provided by unsaturated mono- or dicarboxylic acids monomers such as those corresponding to the formula (II):

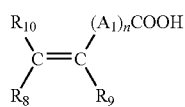

(II)

in which:

n is an integer from 0 to 10, $A_1$ denotes a methylene group, optionally connected to the carbon atom of the unsaturated group, or to the neighboring methylene group when n is greater than 1, via a hetero atom such as oxygen or sulphur, $R_{10}$ denotes a hydrogen atom or a phenyl or benzyl group, $R_8$ denotes a hydrogen atom or a lower alkyl or carboxyl group, and $R_9$ denotes a hydrogen atom, a lower alkyl group or a —$CH_2$—COOH, phenyl or benzyl group.

In the abovementioned formula, a lower alkyl radical preferably denotes a group having 1 to 4 carbon atoms and in particular methyl and ethyl.

The anionic styling polymers containing carboxylic groups which can be used according to the invention are:

A) Homo- or copolymers of acrylic or methacrylic acid or salts thereof and in particular the products sold under the names VERSICOL E or K by the company Allied Colloid and ULTRAHOLD by the company BASF. The copolymers of acrylic acid and of acrylamide sold in the form of their sodium salt under the names RETEN 421, 423 or 425 by the company Hercules, the sodium salts of polyhydroxycarboxylic acids.

B) Copolymers of acrylic or methacrylic acids with a monoethylenic monomer such as ethylene, styrene, vinyl esters, acrylic acid esters or methacrylic acid esters. These copolymers can be grafted onto a polyalkylene glycol such as polyethylene glycol and optionally crosslinked. Mention may be made in particular of the copolymers containing an optionally N-alkylated and/or hydroxyalkylated acrylamide unit in their chain sold under the name QUADRAMER by the company American Cyanamid. Mention may also be made of copolymers of acrylic acid and of $C_1$-$C_4$ alkyl methacrylate and terpolymers of vinylpyrrolidone, of (meth)acrylic acid and of (meth)acrylate of $C_1$-$C_{20}$ alkyl, for example lauryl (such as the product sold by the company ISP under the name ACRYLIDONE LM), tert-butyl (LUVIFLEX VBM 70 sold by BASF) or methyl (STEPANHOLD EXTRA sold by Stepan) and methacrylic acid/ethyl acrylate/tert-butyl acrylate terpolymers such as the product sold under the name LUVIMER 100 P by the company BASF.

C) Copolymers derived from crotonic acid such as those containing vinyl acetate or propionate units in their chain and optionally other monomers such as allylic esters or methallylic esters, vinyl ether or vinyl ester of a linear or branched saturated carboxylic acid with a long hydrocarbon chain such as those containing at least 5 carbon atoms, it being possible for these polymers optionally to be grafted and crosslinked, or alternatively a vinyl, allylic or methallylic ester of an α- or β-cyclic carboxylic acid. Commercial products falling into this class are the resins 28-29-30, 26-13-14 and 28-13-10 sold by the company National Starch.

D) Copolymers derived from $C_4$-$C_8$ monounsaturated carboxylic acids or anhydrides selected from:
 (a) copolymers comprising:
  i one or more maleic, fumaric or itaconic acids or anhydrides and
  ii at least one monomer selected from vinyl esters, vinyl ethers, vinyl halides, phenylvinyl derivatives, acrylic acid and its esters, the anhydride functions of these copolymers optionally being monoesterified or monoamidated. Commercially available examples thereof include, but are not limited to, GANTREZ AN or ES and AVANTAGE CP and Aquaflex FX-64 from the company ISP;

(b) copolymers comprising:
i one or more maleic, citraconic or itaconic anhydrides and
ii one or more monomers selected from allylic or methallylic esters optionally containing one or more acrylamide, methacrylamide, α-olefin, acrylic or methacrylic ester, acrylic or methacrylic acid or vinylpyrrolidone groups in their chain, the anhydride functions of these copolymers optionally being monoesterified or monoamidated.

E) Polyacrylamides containing carboxylate groups.

The polymers comprising sulphonic groups are polymers containing vinylsulphonic, styrenesulphonic, naphthalenesulphonic or acrylamidoalkylsulphonic units.

These polymers can be selected in particular from:
polyvinylsulphonic acid salts having a weight-average molecular weight ranging from approximately 1000 to approximately 100,000, as well as the copolymers with an unsaturated comonomer such as acrylic or methacrylic acids and their esters, as well as acrylamide or its derivatives, vinyl ethers and vinylpyrrolidone; polystyrenesulphonic acid salts, the sodium salts having a weight-average molecular weight of about 500,000 and about 100,000, which are sold respectively under the names FLEXAN 500 and FLEXAN 130 by National Starch. One example thereof is polyacrylamidoethylpropanesulphonic acid sold under the name COSMEDIA POLYMER HSP 1180 by Henkel.

Anionic styling polymers may be also be sulphonated polyesters comprising repeating units representable by the following general formula:

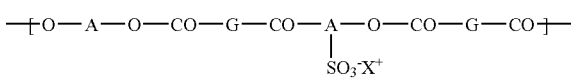

in which A and G represent divalent radicals and X represents an alkali metal, especially sodium or potassium. Among the preferred sulphonated polyesters according to the invention, A represents an arylene radical, especially phenylene, and G represents a linear or branched alkylene radical optionally interrupted by one or more oxygen atoms, or a cycloalkylene radical. When G represents a linear or branched alkylene radical optionally interrupted by one or more oxygen atoms, the radical —O-G-O— is preferably a (poly)alkylene glycol residue containing 1 to 20 alkylene glycol units. The alkylene radical is preferably, according to the invention, a lower, linear or branched $C_2$-$C_4$ alkylene radical, more preferably an ethylene radical Among these polymers, preference will be given to those marketed under the names AQ 1045, AQ 1350 and AQ 14000 by the company EASTMAN CHEMICAL, more particularly AQ 1350.

According to the invention the anionic styling polymers are selected from acrylic acid copolymers such as the acrylic acid/ethyl acrylate/N-tert-butylacrylamide terpolymers sold in particular under the name ULTRAHOLD STRONG by the company BASF, copolymers derived from crotonic acid such as the vinyl acetate/vinyl tert-butylbenzoate/crotonic acid terpolymers and the crotonic acid/vinyl acetate/vinyl neododecanoate terpolymers sold in particular under the name RESIN 28-29-30 by the company National Starch, polymers derived from maleic, fumaric or itaconic acids or anhydrides with vinyl esters, vinyl ethers, vinyl halides, phenylvinyl derivatives or acrylic acid and its esters, such as the methyl vinyl ether/maleic anhydride monoesterified copolymers sold, for example, under the name GANTREZ by the company ISP, the copolymers of methacrylic acid and of methyl methacrylate sold under the name EUDRAGIT L by the company Rohm Pharma, the copolymers of methacrylic acid/methyl methacrylate/$C_1$-$C_4$ alkyl acrylate/acrylic acid or $C_1$-$C_4$ hydroxyalkyl methacrylate which are sold in the form of dispersions under the name AMERHOLD DR 25 by the company Amerchol or under the name ACUDYNE 255 by the company Rohm & Haas, the copolymers of methacrylic acid and of ethyl acrylate sold under the name LUVIMER MAEX or MAE by the company BASF and the vinyl acetate/crotonic acid copolymers and the vinyl acetate/crotonic acid copolymers grafted with polyethylene glycol, sold under the name ARISTOFLEX A by the company BASF.

The anionic styling polymers which are more preferred are selected from the monoesterified methyl vinyl ether/maleic anhydride copolymers sold under the name GANTREZ ES 425 by the company ISP, the acrylic acid/ethyl acrylate/N-tert-butylacrylamide terpolymers sold under the name ULTRAHOLD STRONG by the company BASF, the copolymers of methacrylic acid and of methyl methacrylate sold under the name EUDRAGIT L by the company Rohm Pharma, the vinyl acetate/vinyl tert-butylbenzoate/crotonic acid terpolymers and the crotonic acid/vinyl acetate/vinyl neododecanoate terpolymers sold under the name RESIN 28-29-30 by the company National Starch, the copolymers of methacrylic acid and of ethyl acrylate sold under the name LUVIMER MAEX or MAE by the company BASF and the vinyl pyrrolidone/acrylic acid/lauryl methacrylate terpolymers sold under the name ACRYLIDONE LM by the company ISP.

The amphoteric styling polymers which can be used in accordance with the invention can be selected from polymers containing units B and C distributed randomly in the polymer chain, in which B denotes a unit derived from a monomer containing at least one basic nitrogen atom and C denotes a unit derived from an acid monomer containing one or more carboxylic or sulphonic groups, or alternatively B and C can denote groups derived from carboxybetaine or sulphobetaine zwitterionic monomers; B and C can also denote a cationic polymer chain containing primary, secondary, tertiary or quaternary amine groups, in which at least one of the amine groups bears a carboxylic or sulphonic group connected via a hydrocarbon radical or alternatively B and C form part of a chain of a polymer containing an α,β-dicarboxylic ethylene unit in which one of the carboxylic groups has been made to react with a polyamine containing one or more primary or secondary amine groups.

The amphoteric styling polymers corresponding to the definition given above which are more particularly preferred are selected from the following polymers:

1) Polymers resulting from the copolymerization of a monomer derived from a vinyl compound bearing a carboxylic group such as, more particularly, acrylic acid, methacrylic acid, maleic acid, α-chloroacrylic acid, and a basic monomer derived from a substituted vinyl compound containing at least one basic atom, such as, more particularly, dialkylaminoalkyl methacrylate and acrylate, dialkylaminoalkylmethacrylamides and -acrylamides.

2) Polymers containing units derived from:
(a) at least one monomer selected from acrylamides and methacrylamides substituted on the nitrogen with an alkyl radical,
(b) at least one acidic comonomer containing one or more reactive carboxylic groups, and
(c) at least one basic comonomer such as esters containing primary, secondary, tertiary and quaternary amine substituents of acrylic and methacrylic acids and the product of quaternization of dimethylaminoethyl methacrylate with dimethyl or diethyl sulphate.

The N-substituted acrylamides or methacrylamides which are more particularly preferred according to the invention are groups in which the alkyl radicals contain from 2 to 12 carbon atoms and more particularly N-ethylacrylamide, N-tert-butylacrylamide, N-tert-octylacrylamide, N-octylacrylamide, N-decylacrylamide, N-dodecylacrylamide and the corresponding methacrylamides.

The acidic comonomers are selected more particularly from acrylic acid, methacrylic acid, crotonic acid, itaconic acid, maleic acid and fumaric acid and alkyl monoesters, having from 1 to 4 carbon atoms, of maleic or fumaric acids or anhydrides.

The preferred basic comonomers are aminoethyl, butylaminoethyl, N,N'-dimethylaminoethyl and N-tert-butylaminoethyl methacrylates.

The copolymers whose CTFA name is octylacrylamide/acrylates/butylaminoethyl methacrylate copolymer such as the products sold under the name AMPHOMER or LOVOCRYL 47 by the company National Starch are particularly used.

3) crosslinked and alkylated polyamino amides partially or totally derived from polyamino amides of formula (III):

$$-[CO-R_{10}-CO-Z]- \quad (III)$$

in which:
$R_{10}$ represents a divalent radical derived from a saturated dicarboxylic acid, a mono- or dicarboxylic aliphatic acid containing an ethylenic double bond, an ester of a lower alkanol, having from 1 to 6 carbon atoms, of these acids or a radical derived from the addition of any one of the acids to a bis(primary) or bis(secondary) amine, and Z denotes a bis(primary), mono- or bis(secondary) polyalkylene-polyamine radical and preferably represents:

(a) in proportions of from 60 to 100 mol %, the radical $$-NH-[(CH_2)_x-NH]_p- \quad (IV)$$

where x=2 and p=2 or 3, or alternatively x=3 and p=2 this radical being derived from diethylenetriamine, from triethylenetetraamine or from dipropylenetriamine;

(b) in proportions of from 0 to 40 mol %, the radical (IV) above in which x=2 and p=1 and which is derived from ethylenediamine, or the radical derived from piperazine:

$$-N\underset{\phantom{x}}{\diagdown}\underset{\phantom{x}}{\diagup}N-$$

(c) in proportions of from 0 to 20 mol %, the $-NH-(CH_2)_6-NH-$ radical derived from hexamethylenediamine, these polyamino amines being crosslinked by addition of a difunctional crosslinking agent selected from epihalohydrines, diepoxides, dianhydrides and bis-unsaturated derivatives, using from 0.025 to 0.35 mol of crosslinking agent per amine group of the polyamino amide and alkylated by the action of acrylic acid, chloroacetic acid or an alkane sultone, or salts thereof.

The saturated carboxylic acids are preferably selected from acids having from 6 to 10 carbon atoms, such as adipic acid, 2,2,4-trimethyladipic acid and 2,4,4-trimethyladipic acid, terephthalic acid, acids containing an ethylenic double bond such as, for example, acrylic acid, methacrylic acid and itaconic acid.

The alkane sultones used in the alkylation are preferably propane sultone or butane sultone, the salts of the alkylating agents are preferably the sodium or potassium salts.

4) polymers containing zwitterionic units of formula (V):

$$R_{11}-\left[\underset{R_{13}}{\overset{R_{12}}{\underset{|}{\overset{|}{C}}}}\right]_y-\underset{R_{15}}{\overset{R_{14}}{\underset{|}{\overset{|}{N^+}}}}-(CH_2)_z-\overset{O}{\underset{\phantom{|}}{\overset{\|}{C}}}-O^- \quad (V)$$

in which:
$R_{11}$ denotes a polymerizable unsaturated group such as an acrylate, methacrylate, acrylamide or methacrylamide group, y and z represent an integer ranging from 1 to 3, $R_{12}$ and $R_{13}$ represent a hydrogen atom, methyl, ethyl or propyl, $R_{14}$ and $R_{15}$ represent a hydrogen atom or an alkyl radical such that the sum of the carbon atoms in $R_{14}$ and $R_{15}$ does not exceed 10.

The polymers comprising such units can also contain units derived from non-zwitterionic monomers such as dimethyl or diethylaminoethyl acrylate or methacrylate or alkyl acrylates or methacrylates, acrylamides or methacrylamides or vinyl acetate.

By way of example, mention may be made of the copolymer of methyl methacrylate/dimethyl carboxymethylammonio methyl ethylmethacrylate such as the product sold under the name DIAFORMER Z301 by the company Sandoz.

5) Polymers derived from chitosan containing monomer units corresponding to the following formulae:

(D)

(E)

(F)

the unit D being present in a concentration ranging from 0 to 30%, the unit E in a concentration ranging from 5 to 50%, and the unit F in a concentration ranging from 30 to 90%, it being understood that, in this unit F, $R_{16}$ represents a radical of formula:

$$R_{17}-\underset{\underset{}{|}}{\overset{\overset{R_{18}}{|}}{C}}-(O)_q-\underset{\underset{}{|}}{\overset{\overset{R_{19}}{|}}{C}}$$

in which, if $q=0$, $R_{17}$, $R_{18}$ and $R_{19}$ each independently represent a hydrogen atom, a methyl, hydroxyl, acetoxy or amino residue, a monoalkylamine residue or a dialkylamine residue which are optionally interrupted by one or more nitrogen atoms and/or optionally substituted with one or more amine, hydroxyl, carboxyl, alkylthio or sulphonic groups, an alkylthio residue in which the alkyl group bears an amino residue, at least one of the radicals $R_{17}$, $R_{18}$ and $R_{19}$ being, in this case, a hydrogen atom;

or, if $q=1$, $R_{17}$, $R_{18}$ and $R_{19}$ each independently represent a hydrogen atom, as well as the salts formed by these compounds with bases or acids.

6) Polymers derived from the N-carboxyalkylation of chitosan, such as N-carboxymethylchitosan or N-carboxybutyl-chitosan sold under the name "EVALSAN" by the company Jan Dekker.

(7) Polymers corresponding to formula (VI):

$$\left[-(\mathrm{CH}-\mathrm{CH}_2)-\underset{\underset{\mathrm{COOH}}{|}}{\mathrm{CH}}-\underset{\underset{\underset{\underset{\underset{R_{22}}{|}}{N-R_{23}}}{|}}{\underset{R_{24}}{|}}}{\underset{N-R_{21}}{\underset{|}{CO}}}\mathrm{CH}-\right]_7 \quad \text{(VI)}$$

(with $R_{20}$ above the first CH)

in which:

$R_{20}$ represents a hydrogen atom, a $CH_3O$, $CH_3CH_2O$ or phenyl radical, $R_{21}$ denotes hydrogen or a lower alkyl radical such as methyl or ethyl, $R_{22}$ denotes hydrogen or a lower alkyl radical such as methyl or ethyl, $R_{23}$ denotes a lower alkyl radical such as methyl or ethyl or a radical corresponding to the formula: $-R_{24}-N(R_{22})_2$, wherein $R_{22}$ can be the same or different, $R_{24}$ representing a $-CH_2-CH_2-$, $-CH_2-CH_2-CH_2-$ or $-CH_2-CH(CH_3)-$ group, and the higher homologues of these radicals containing up to 6 carbon atoms.

8) Amphoteric polymers of the type -D-X-D-X selected from:

(a) polymers obtained by the action of chloroacetic acid or sodium chloroacetate on compounds containing at least one unit of formula:

-D-X-D-X-D-  (VII)

where D denotes a radical $$-N\underset{\underset{}{\diagdown\diagup}}{\diagup\diagdown}N-$$

and X denotes the symbol E or E', E or E', which may be identical or different, denotes a divalent radical which is an alkylene radical containing a straight or branched chain containing up to 7 carbon atoms in the main chain, which is unsubstituted or substituted with hydroxyl groups and which can contain, in addition to the oxygen, nitrogen and sulphur atoms, from 1 to 3 aromatic and/or heterocyclic rings; the oxygen, nitrogen and sulphur atoms being present in the form of ether, thioether, sulphoxide, sulphone, sulphonium, alkylamine or alkenylamine groups, hydroxyl, benzylamine, amine oxide, quaternary ammonium, amide, imide, alcohol, ester and/or urethane groups.

(b) Polymers of formula:

-D-X-D-X-  (VII)

in which D denotes a radical $$-N\underset{\underset{}{\diagdown\diagup}}{\diagup\diagdown}N-$$

and X denotes the symbol E or E' and at least once E', E having the meaning given above and E' is a divalent radical which is an alkylene radical with a straight or branched chain having up to 7 carbon atoms in the main chain, which is unsubstituted or substituted with one or more hydroxyl radicals and containing one or more nitrogen atoms, the nitrogen atom being substituted with an alkyl chain which is optionally interrupted by an oxygen atom and necessarily containing one or more carboxyl functions or one or more hydroxyl functions and betainized by reaction with chloroacetic acid or sodium chloroacetate.

9) $(C_1-C_5)$alkyl vinyl ether/maleic anhydride copolymers partially modified by semiamidation with an N,N-dialkylaminoalkylamine such as N,N-dimethylaminopropylamine or by semiesterification with an N,N-dialkanolamine. These copolymers can also contain other vinyl comonomers such as vinylcaprolactam.

The amphoteric styling polymers which are particularly preferred according to the invention are those of family (3), such as the copolymers whose CTFA name is octylacrylamide/acrylates/butylaminoethyl methacrylate copolymer, such as the products sold under the names AMPHOMER, AMPHOMER LV 71 or LOVOCRYL 47 by the company National Starch and those of family (4) such as the copolymer of methyl methacrylate/dimethyl carboxymethylammonio methyl ethylmethacrylate, sold, for example, under the name DIAFORMER Z301 by the company Sandoz.

The anionic or amphoteric styling polymers can, if necessary, be partially or totally neutralized. The neutralizing agents are, for example, sodium hydroxide, potassium hydroxide, 2-amino-2-methyl-1-propanol, monoethanolamine, triethanolamine or triisopropanolamine and inorganic or organic acids such as hydrochloric acid or citric acid.

The nonionic styling polymers useful according to the present invention are polyurethanes and N-vinylpyrrolidone polymers and copolymers. Nonionic polymers containing N-vinylpyrrolidone in various weight average molecular weights are available commercially from ISP Corporation—specific examples of such materials are homopolymers of N-vinylpyrrolidone having an average molecular weight of about 630,000 sold under the name PVP K-90 and are homopolymers of N-vinylpyrrolidone having an average molecular weight of about 1,000,000 sold under the name of PVP K-120.

Particularly preferred styling polymers are polyvinylpyrrolidone, vinylpyrrolidone/vinyl acetate copolymer, AMP-acrylates/allyl methacrylate copolymer (commercially available from Noveon under the tradename, Fixate G-100), sodium polystyrene sulfonate (commercially available from National Starch under the tradename, Flexan II), Vinylpyrrolidone/acrylates/lauryl methacyrlate copolymer (commercially available from ISP under the tradename, Acrylidone LM), polyquaternium-6, and polyurethane-2 (commercially available from Noveon under the tradename, Avalure 405 or 410).

The styling polymer is present in the compositions of the present invention at a level of from 0.1% to 15% by weight, preferably at a level of from 0.1% to 10% by weight, and even more preferably at a level from 0.5% to 5.0% by weight, based on the weight of the composition. The mass average molecular weight of the polymer is not critical, but is generally in the range of from about 2,000 to about 2,000,000.

Emulsifying Agents

Emulsifiers or dispersing agents, include, without limitation, any which are compatible with the solvent and elastomers used. The emulsifying agents which can be used according to the invention are those having an HLB of less than 7 and in particular fatty acid esters of polyols such as mono-, di-, tri- or sesqui-oleates or -stearates of sorbitol or glycerol, laurates of glycerol or polethylene glycol; alkyl or alkoxy dimethicone copolyols having an alkyl or alkoxy chain pendent or at the end of a silicone-based backbone having for example from 6 to 22 carbon atoms. The emulsifying agents may also be those having an HLB greater than 7 such as fatty acid esters of polyethylene glycol (monostearate or monolaurate of polyethylene glycol); esters of fatty acids (stearate, oleate) of sorbitol which are polyoxyethylenated; polyoxy ethylenated alkyl (lauryl, cetyl, stearyl, octyl) ethers and dimethicone copolyols. In general, it is possible to use nonionic or anionic or cationic emulsifiers well known to persons skilled in the art.

The nonionic type emulsifiers are fatty acids or amides of polyalkoxylated and/or polyglycerolated fatty acids; polyoxyethylenated and/or polyoxypropylenated fatty alcohols (i.e., compounds prepared by reacting an aliphatic fatty alcohol such as behenyl or cetyl alcohol with ethylene oxide or propylene oxide or an ethylene oxide/propylene oxide mixture); fatty acid esters of polyols, optionally polyoxyethylenated and/or polyoxypropylenated (i.e., compounds prepared by reacting a fatty acid such as stearic acid or oleic acid with a polyol such as, for example, an alkylene glycol or glycerol or a polyglycerol, optionally in the presence of ethylene oxide or propylene oxide or an ethylene oxide/propylene oxide mixture); and polyalkoxylated and/or polyglycerolated alkylphenols; or polyalkoxylated and/or polyglycerolated 1,2- or 1,3-alkanediols; and alkylethers of polyalkoxylated and/or polyglycerolated 1,2- or 1,3-alkanediols or alkenediols, or mixtures thereof.

The polyalkoxylated fatty acids are commercial products, and are principally products sold under the mark "Myrj".

The esters of fatty acids and polyoxyethylenated polyols for which the polyol is sorbitol are known products (Polysorbate and products sold under the mark "Tween").

The polyoxyethylenated fatty alcohols are commercial products and principally those sold under the mark "Brij".

The fatty acids or amides of polyglycerolated fatty acids are also commercial products such as those sold under the mark "Plurol" (Gattefosse) or "Drewpol" (Stefan Company).

The emulsifying agents according to the invention can also be anionic surfactants which may have a hydrophilic-lipophilic balance (HLB) ranging from 10 to 40. They are principally salts of fatty acids (for example alkaline salts or organic salts such as amine salts), the said fatty acids having, for example, from 12 to 18 carbon atoms and being able to have a double bond as in the case of oleic acid; the alkaline salts or salts of organic bases of alkyl-sulfuric and alkyl-sulfonic acids having 12 to 18 carbon atoms, of alkyl-aryl-sulfonic acids whose alkyl chain contains 6 to 16 carbon atoms, the aryl group being, for example, a phenyl group. They are also ether-sulfates, in particular, the sulfatation products of fatty alcohols and polyalkoxylated alkylphenols, in which the aliphatic chain has from 6 to 20 carbon atoms and the polyalkoxylated chain has from 1 to 30 oxyalkylene units, in particular oxyethylene, oxypropylene or oxybutylene. All these anionic surfactants are well known and many among them are commercial products.

The emulsifying agents according to the invention can also be cationic surfactants such as quaternary ammonium derivatives.

The emulsifying agent is present in the composition in an amount of from 0.05% to 15% by weight, preferably in an amount of from 0.1% to 10% by weight, and more preferably in an amount of from 0.5% to 6.0% by weight, based on the weight of the composition. Particularly preferred emulsifying agents are Isoceteth-20, Polysorbate 20, PEG-40 hydrogenated castor oil, oleth-2, laureth-7, cetyl alcohol and glyceryl stearate.

Cosmetically-Acceptable Co-Solvent

The amount of co-solvent used in accordance with the present invention must be sufficient to completely solubilize, suspend or disperse the necessary ingredients. The amount of co-solvent used may also depend on whether or not the solvent is volatile and what other ingredients are intended as well as the final hardness, viscosity, specific gravity or other desirable properties of the cosmetic base or composition. Generally, the balance of the formulation will be co-solvent, however, the amount of co-solvent can range as high as 95% by weight. And while it is difficult to identify a minimum amount of co-solvent as it will depend on a number of factors including the number and amount of other ingredients contained within the formulation, generally at least 20% of each formulation will be co-solvent by weight. Preferably the amount of co-solvent ranges from 30% to 80% by weight.

The cosmetically acceptable co-solvent of the composition is preferably an aqueous medium consisting of water and may advantageously comprise at least one cosmetically acceptable organic solvent such as, for example, alcohols such as ethyl alcohol, isopropyl alcohol, benzyl alcohol, phenylethyl alcohol, and mixtures of all these compounds may also be used as the co-solvent.

It has been found by the inventors that the use of a composition utilizing the non-aqueous polar solvent in combination with the silicone elastomer, on keratinous material such hair, resulted in a medium to light styling hold, a unique, soft and dry feel to and reshapability of said keratinous material without the need to re-apply said cosmetic composition and/or heat.

Optional Ingredients/Additives

The composition of the present invention can also comprise hair-conditioning agents. Conditioning agents can be selected from oily substances, silicones, non-ionic substances, cationic amphiphilic ingredients, cationic polymers or their mixtures. Oily substances are selected from compounds such as silicone oils, either volatile or non-volatile, natural and synthetic oils. Silicone oils that can be used include dimethicone, dimethiconol, polydimethylsiloxane, DC fluid ranges from Dow Corning, natural oils such as olive oil, almond oil, avocado oil, weizenkeim oil, ricinus oil and the synthetic oils, such as mineral oil.

Silicones that can be used as conditioning agents are dimethicone, cyclopentasiloxane, cyclohexasiloxane, amodimethicone, silicone emulsions, and dimethicone copolyols.

Non-ionic conditioning agents can be polyols such as glycerin, glycol and derivatives, polyethyleneglycols known with trade names Carbowax PEG from Union Carbide and Polyox WSR range from Amerchol, polyglycerin, polyethyleneglycol mono or di fatty acid esters. Non-ionic conditioning agents can also be esters and hydrocarbons such as caprylic/capric triglycerides, isopropyl palmitate, isododecane, polyisobutene.

Cationic amphiphilic conditioning agents ingredients can also be used. Typical examples of those ingredients are cetyl trimethly ammonium chloride, stear trimonium chloride, dipalmitoyl dimonium chloride, distearyl dimethyl ammonium chloride, stearamidopropyl trimonuim chloride, dioleoylethyl dimethyl ammonium methosulfate, dioleoylethyl hydroxyethylmonium methosulfate. Those can at the same time serve as solubilizing agents for those ingredients difficult to integrate into the formulations.

The cationic polymers mentioned above used for achieving styling are as well found to be suitable for hair conditioning purposes when formulated into the compositions of the present invention.

Typical concentration range for any of the conditioners mentioned above can be from 0.01% to 5% by weight, preferably from 0.01% to 3.5% by weight, and more preferably from 0.05% to 2.5% by weight, based on the weight of the composition.

The composition(s) of the present invention may also comprise additives, for instance those chosen from the non-exhaustive list such as reducing agents, antioxidants, sequestering agents, softeners, antifoams, moisturizers, emollients, basifying agents, gelling agents, wetting agents, thickening agents, spreading agents, dispersants, plasticizers, sunscreens, direct dyes or oxidation dyes, pigments, mineral fillers, clays, colloidal minerals, nacres, nacreous agents, fragrances, peptizers, preserving agents, fixing or non-fixing polymers, ceramides, proteins, antioxidants, active agents, vitamins, antidandruff agents, aliphatic or aromatic alcohols, and more particularly ethanol, benzyl alcohol, modified or unmodified polyols, such as glycerol, glycol, propylene glycol, dipropylene glycol, butylene glycol or butyl diglycol, volatile silicones, mineral, organic or plant oils, oxyethylenated or non-oxyethylenated waxes, paraffins, fatty acids, associative or non-associative thickening polymers, fatty amides, fatty esters, fatty alcohols, and the like.

The compositions of the present invention may also contain one or more waxes to modify viscosity, feel or stability. Waxes are lower-melting organic mixtures or compounds of high molecular weight, solid at room temperature and generally similar in composition to fats and oils except that they contain no glycerides. They can be hydrocarbons, esters of fatty acids or alcohols. Waxes useful in the present invention are selected from the group consisting of animal waxes, vegetable waxes, mineral waxes, natural waxes, synthetic waxes, petroleum waxes, ethylenic polymers, hydrocarbons, silicone waxes, and mixtures thereof.

According to one embodiment of the present invention, there is provided a process for treating keratinous materials, such as hair, by applying the above-disclosed composition onto the keratinous material. The precise amount of composition to be applied onto the material will depend on the degree of treatment desired.

The following examples further describe and demonstrate embodiments within the scope of the present invention. The examples are given solely for the purpose of illustration and are not to be construed as limitations of the present invention, as many variations thereof are possible without departing from the spirit and scope of the invention. All exemplified amounts are concentrations by weight of the total composition, unless otherwise specified.

EXAMPLE

Example 1

Hair Styling Gel

| CHEMICAL OR INCI NAME | % |
| --- | --- |
| DIMETHICONE/VINYL DIMETHICONE CROSSPOLYMER | 3.25 |
| PROPYLENE GLYCOL | 24.0 |
| HEXYLENE GLYCOL | 8.0 |
| CYCLOPENTASILOXANE | 12.0 |
| POLYVINYLPYRROLIDONE | 0.5 |
| POLYACRYLAMIDE | 1.4 |
| LAURETH-4 | 0.25 |
| C13–14 ISOPARAFFIN | 0.74 |
| PRESERVATIVES, FRAGRANCES, OTHER ADDITIVES | 2.0 |
| WATER | q.s. to 100% |

What is claimed is:

1. A process for styling a keratinous material comprising:
   (a) providing a composition containing:
      i. at least one silicone elastomer;
      ii. at least about 20% by weight of at least one non-aqueous polar solvent, based on the total weight of the composition;
      iii. optionally, at least one styling polymer;
      iv. optionally, at least one emulsifying agent; and
      v. a cosmetically acceptable co-solvent, other than (ii), and
   (b) applying said composition onto the keratinous material, wherein the keratinous material is hair on the head; and wherein the composition is used for styling the hair.

2. The process of claim 1 wherein the at least one silicone elastomer is present in amount of from about 0.1% to about 25% by weight, based on the weight of the composition.

3. The process of claim 1 wherein the at least one silicone elastomer is present in amount of from about 0.5% to about 5% by weight, based on the weight of the composition.

4. The process of claim 1 wherein the at least one silicone elastomer is a dimethicone/vinyldimethicone crosspolymer.

5. The process of claim 1 wherein the at least one non-aqueous polar solvent is present in amount of up to about 75% by weight, based on the weight of the composition.

6. The process of claim 1 wherein the at least one non-aqueous polar solvent is present in amount of from about 20% to about 50% by weight, based on the weight of the composition.

7. The process of claim 1 wherein the at least one non-aqueous polar solvent is chosen from glycols and glycol ethers.

8. The process of claim 1 wherein the at least one styling polymer is present in an amount of from about 0.1% to about 15% by weight, based on the weight of the composition.

9. The process of claim 1 wherein the at least one styling polymer is present in an amount of from about 0.1% to about 5% by weight, based on the weight of the composition.

10. The process of claim 1 wherein the at least one styling polymer is a water-soluble or water-dispersible polymer chosen from are polyvinylpyrrolidone, vinylpyrrolidone/vinyl acetate copolymer, AMP-acrylates/allyl methacrylate copolymer, sodium polystyrene sulfonate, Vinylpyrrolidone/acrylates/lauryl methacyrlate copolymer, polyquaternium-6, and polyurethane-2, and mixtures of said styling polymers.

11. The process of claim 1 wherein the at least one emulsifying agent is present in an amount of from about 0.05% to about 15% by weight, based on the weight of the composition.

12. The process of claim 1 wherein the at least one emulsifying agent is present in amount of from about 0.5% to about 6% by weight, based on the weight of the composition.

13. A process for styling a keratinous material comprising:
   (a) providing a composition containing:
      i. from about 0.5% to about 5% by weight of at least one non-emulsifying silicone elastomer;
      ii. from about 20% to about 50% by weight of at least one non-aqueous polar solvent chosen from glycols and glycol ethers;
      iii. from about 0.1% to about 5% by weight of at least one styling polymer;
      iv. from about 0.5% to about 6% by weight of at least one emulsifying agent;
      v. and remainder, to 100%, of a cosmetically acceptable co-solvent, other than (ii), all weights being based on the total weight of the composition, and
   (b) applying said composition onto the keratinous material, wherein the keratinous material is hair on the head; and wherein the composition is used for styling the hair.

* * * * *